(12) United States Patent
Nino et al.

(10) Patent No.: US 9,549,745 B2
(45) Date of Patent: Jan. 24, 2017

(54) DELIVERY DEVICES AND SYSTEMS FOR TOOLS USED IN MEDICAL PROCEDURES

(75) Inventors: John Nino, Simi Valley, CA (US); David Ivinson, Camarillo, CA (US); Douglas Slomski, Chicago, IL (US)

(73) Assignee: ECA Medical Instruments, Newbury Park, CA (US)

( * ) Notice: Subject to any disclaimer, the term of this patent is extended or adjusted under 35 U.S.C. 154(b) by 736 days.

(21) Appl. No.: 13/820,057

(22) PCT Filed: Jul. 11, 2012

(86) PCT No.: PCT/US2012/046292
§ 371 (c)(1),
(2), (4) Date: Apr. 26, 2013

(87) PCT Pub. No.: WO2013/009900
PCT Pub. Date: Jan. 17, 2013

(65) Prior Publication Data
US 2013/0226182 A1    Aug. 29, 2013

Related U.S. Application Data

(60) Provisional application No. 61/507,053, filed on Jul. 12, 2011.

(51) Int. Cl.
| | |
|---|---|
| A61B 17/16 | (2006.01) |
| A61B 17/32 | (2006.01) |
| A61B 17/3201 | (2006.01) |
| A61B 17/34 | (2006.01) |
| A61B 17/00 | (2006.01) |

(52) U.S. Cl.
CPC ....... *A61B 17/1671* (2013.01); *A61B 17/3201* (2013.01); *A61B 17/320016* (2013.01); *A61B 17/3421* (2013.01); *A61B 2017/00261* (2013.01); *A61B 2017/00867* (2013.01)

(58) Field of Classification Search
CPC ............... A61B 17/3207; A61B 17/32075; A61B 2017/320733; A61B 17/32002; A61B 2017/320052; A61B 2017/32006
USPC ................ 606/167, 170, 174, 180
See application file for complete search history.

(56) References Cited

U.S. PATENT DOCUMENTS

| | | |
|---|---|---|
| 5,451,227 A | 9/1995 | Michaelson |
| 5,707,350 A | 1/1998 | Krause et al. |
| 5,895,389 A * | 4/1999 | Schenk .................. A61B 17/17 606/102 |

(Continued)

FOREIGN PATENT DOCUMENTS

| | | |
|---|---|---|
| EP | 1854587 A1 | 11/2007 |
| EP | 1929975 A1 | 6/2008 |

(Continued)

*Primary Examiner* — Anu Ramana
(74) *Attorney, Agent, or Firm* — Baker & Hostetler LLP (57) ABSTRACT

A device and method of delivering a medical tool which may be a memory resector, cutter, probe, or the like, including a memory blade compacted in a small diameter state which expands in a relaxed memory state is disclosed. Said delivery may include using a hollow sheath to pre-compact or preload a memory blade into a compact position, transferring said compacted memory blade into a cannula, and deploying said memory blade from the distal end of said cannula whereby the memory blade returns to its normal expanded memory state.

10 Claims, 9 Drawing Sheets

(56) References Cited

U.S. PATENT DOCUMENTS

| | | | |
|---|---|---|---|
| 6,740,090 B1 * | 5/2004 | Cragg | A61B 17/1617 128/898 |
| 6,923,813 B2 | 8/2005 | Phillips et al. | |
| 6,960,206 B2 | 11/2005 | Keane | |
| 7,175,626 B2 | 2/2007 | Neff | |
| 7,255,703 B2 | 8/2007 | Mujwid et al. | |
| 7,296,500 B1 | 11/2007 | Martinelli | |
| 7,699,852 B2 | 4/2010 | Frankel et al. | |
| 7,749,251 B2 | 7/2010 | Obenchain et al. | |
| 7,762,164 B2 | 7/2010 | Nino et al. | |
| 7,938,046 B2 | 5/2011 | Nino et al. | |
| 2002/0049449 A1 | 4/2002 | Bhatnagar et al. | |
| 2003/0191474 A1 | 10/2003 | Cragg et al. | |
| 2005/0107800 A1 | 5/2005 | Frankel et al. | |
| 2005/0240193 A1 | 10/2005 | Layne et al. | |
| 2006/0241629 A1 | 10/2006 | Krebs et al. | |
| 2007/0006692 A1 | 1/2007 | Phan | |
| 2007/0066977 A1 * | 3/2007 | Assell | A61B 17/1757 606/96 |
| 2007/0260227 A1 | 11/2007 | Phan | |
| 2007/0260257 A1 | 11/2007 | Phan | |
| 2008/0300510 A1 | 12/2008 | Schwyn et al. | |
| 2009/0194446 A1 | 8/2009 | Miller et al. | |
| 2009/0198245 A1 | 8/2009 | Phan | |
| 2009/0306657 A1 | 12/2009 | Piippo et al. | |
| 2010/0082033 A1 | 4/2010 | Germain | |
| 2010/0121332 A1 | 5/2010 | Crainich et al. | |
| 2010/0204693 A1 | 8/2010 | Sanders et al. | |
| 2010/0268234 A1 | 10/2010 | Aho et al. | |
| 2011/0060369 A1 | 3/2011 | Assell et al. | |
| 2011/0098709 A1 | 4/2011 | Malandain et al. | |
| 2011/0144671 A1 | 6/2011 | Piippo et al. | |

FOREIGN PATENT DOCUMENTS

| | | |
|---|---|---|
| WO | WO 01/39930 A1 | 6/2001 |
| WO | WO 03/017857 | 3/2003 |
| WO | WO 2005/077603 A1 | 8/2005 |
| WO | WO 2008/075186 A3 | 6/2008 |

* cited by examiner

DELIVERY DEVICES AND SYSTEMS FOR TOOLS USED IN MEDICAL PROCEDURES

RELATED APPLICATION

This application claims the full Paris Convention benefit of and priority to U.S. Provisional Patent Application Ser. No. 61/507,053 filed Jul. 12, 2011, the contents of which is incorporated by reference herein in its entirety, as if fully set forth herein.

BACKGROUND

1. Field

This disclosure relates to a delivery device, method, and system for tools used in medical procedures.

2. General Background

Figure 1A:
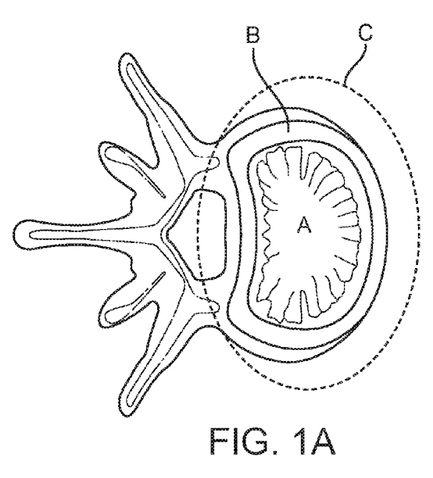
FIGS. 1A and 1B are top and side views of a vertebral body.
Figure 1B:
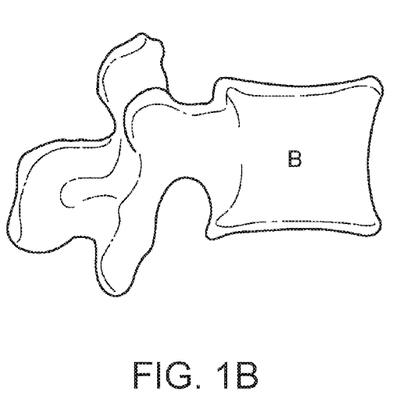
Figure 2A:
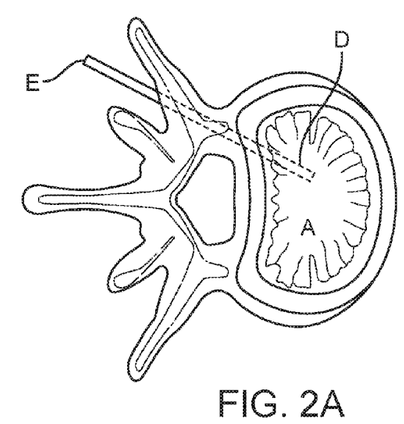
FIGS. 2A and 2B are top and side views of a trocar and/or cannula introduced through a vertebral body into cancelleous bone.
Figure 2B:
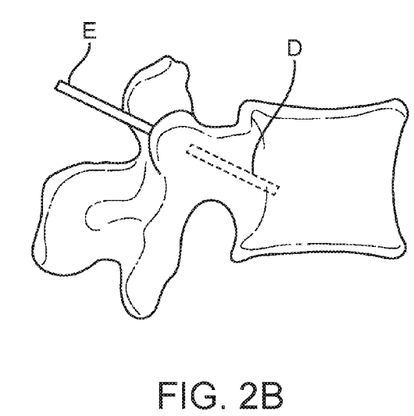

Within a vertebra is cancelleous bone "A," see FIGS. 1 and 2. Surrounding the cancellous bone is a Cortical rim "B," which is compared to compact bone. Compared to compact bone, cancellous has a higher surface area but is less dense, softer, weaker, and less stiff. It typically occurs at the ends of long bones, proximal to joints and within the interior of vertebrae. Cancellous bone is highly vascular and frequently contains red bone marrow where hematopoiesis, the production of blood cells, occurs. The primary anatomical and functional unit of cancellous bone is the trabecula. The vertebral body "C" includes both compact and cancellous bone.

One method to access the cancelleous bone of a vertebra is by way of a trocar "D." A trocar is a sharply pointed shaft, usually with a three-sided point. A trocar may be used within a cannula "E," a hollow tube, designed to be inserted into a vein, artery, bone marrow or body cavity. The word trocar is derived from the French "trois" (three)+"carre" (side).

Procedures used to address damage to vertebral bodies may include vertebroplasty and kyphoplasty, which are medical spinal procedures where bone cement is injected into a damaged or fractured vertebra with the goal of relieving the pain of osteoporotic compression fractures.

Vertebroplasty is typically performed by a spine surgeon or interventional radiologist. It is a minimally invasive procedure and patients usually go home on the same or next day as the procedure. Patients are given local anesthesia and light sedation for the procedure, though it can be performed using only local anesthetic for patients with medical problems who cannot tolerate sedatives well.

During a procedure, bone cement is injected with a biopsy needle into the collapsed or fractured vertebra. Access to the cancelleous bone is via a needle through a resected hole. The bone cement dries and may form a support structure within the vertebra that provides stabilization and strength.

SUMMARY

A method of delivering a tool which may be a memory resector, cutter, probe or the like, including a memory blade preloaded into a hollow sheath; said memory tool in some aspects having a blade which is compacted into said hollow sheath; a hollow cannula with an i.d. substantially the same as the i.d. of said hollow sheath; and, aligning the hollow sheath with the cannula and passing the compacted blade resecting tool, in a compacted state into said cannula. Said method may further comprise deploying said memory tool from the distal end of said cannula, whereby the memory tool returns to its normal memory state.

A method of delivering a tool, including at least two memory blades preloaded into a hollow sheath; said memory tool in some aspects having a blade which is compacted into said hollow sheath; a hollow cannula with an i.d. substantially the same as the i.d. of said hollow sheath; and, aligning the hollow sheath with the cannula and passing the compacted blade resecting tool, in a compacted state into said cannula. Said method may further comprise deploying said memory tool from the distal end of said cannula whereby the blades expand to a diameter larger than said i.d.

A method of delivering a tool, including at least a blade preloaded into a hollow sheath; said memory tool in some aspects having a blade which is compacted into said hollow sheath; a hollow cannula with an i.d. substantially the same as the i.d. of said hollow sheath; and, aligning the hollow sheath with the cannula and passing the compacted blade resecting tool, in a compacted state into said cannula. Said method may further comprise deploying said memory tool from the distal end of said cannula whereby the blades expand to a diameter larger than said i.d.

A resecting tool comprising a blade body assembly with a proximal and a distal end; a probe with a flat surface formed at the distal end of said blade body assembly; a memory blade with a substantially flat surface formed at the distal end of said blade body assembly and proximate to said probe; a memory orientation whereby in a compacted state the distal edge of said memory blade is generally aligned with said probe and in a relaxed or expanded state said distal edge rotates in a scissor-like fashion downward or upward from the distal edge of the probe.

A resecting tool comprising a blade body assembly with a proximal and a distal end; a first memory baled with a flat surface and a cutting surface or edge formed at the distal end of said blade body assembly; a second memory baled with a flat surface and a cutting surface or edge formed at the distal end of said blade body assembly; a memory orientation whereby in a compacted state the distal edges of said memory blades may be compacted to fit within the i.d. of a hollow sheath that has the same i.d. as a cannula. The memory state of said blades being adjacent flat surfaces and separated distal tips. When going from compacted to relaxed (expanded state) said distal edges rotate apart in a scissor like fashion downward or upward, each pivoting from the blade body assembly where they are attached. Upon compaction, the blades slide against each other, rotating shut and in doing so can scrape off debris that might otherwise block withdrawal into a cannula.

DRAWINGS

The above-mentioned features of the present disclosure will become more apparent with reference to the following description taken in conjunction with the accompanying drawings wherein like reference numerals denote like elements and in which.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

According to some aspects of exemplary implementations, as shown in FIGS. 3A through 3D, a sequence of loading one or more memory resector blades 10 or other resecting or cutting tool into a specific i.d. cannula are shown. Unloaded said resector blades have expanded memory define shape and diameter 11. To maximize the size of a memory resector blade to be loaded into and then deployed through a cannula, said memory resector blade is pre-loaded into a movable sheath 100 wherein the memory blade is collapsed (also referred to as compacted) for insertion into a cannula 200 which has an inner guide pathway 202. Compaction is preferable to a diameter "ds" which is substantially as large as provides as a known inside diameter (i.d.) 210 cannula 200. Although less preferable, it is also possible to make the blades smaller and compact them to a size smaller than the i.d. 210 of the cannula. In all instances, the blade body assembly is a limiting factor and its o.d. 25 must allow passage into said cannula 200 to allow for movement.

The proximal end of the blade body assembly may be affixed permanently into the handle (which may also be a torque limiting device). Alternatively the blade body assembly may be removably affixed, a snap in fit, a snap into fit or a pressure fit. In some instance a lumen 22 may be formed through said handle in fluid communication with a lumen in said blade body assembly 27 whereby fluid communication near the distal end 13 of the blade body assembly 13 and/or blades 10 may occur. Those of ordinary skill in the art will recognize that said fluid communication provides for such interactions as aspiration, irrigation, addition of chemicals, cement, antibiotics and removal of resected material.

The resector blade(s) 10 in this implementation is affixed to the distal end 13 of blade body assembly 15. In some instances the blade body assembly may be attached at its proximal end 17 to a handle 20 to provide control and movement. In some instances the compaction of said blades may be to a diameter equal to the outer diameter o.d. 25 of the blade body assembly.

In some instance the handle 20 may further comprise a torque limiting device whereby deployed resector blades are rotated or moved during operation (to resect tissue or bone) with a force that is less than the force which is likely to break the blade(s).

The hollow sheath 100 has a distal end 105 and a flanged proximal end 110. The memory resector blades 10 are compacted and fitted into said sheath 100 via the proximal end 110. The hollow sheath has an annular wall which defines a blade guide 115 therethrough. While confined to the blade guide 115 the memory resector blades remain compacted, when the sheath is moved laterally from the distal end of the blade body assembly 13 towards the proximal end 17 of the blade body assembly said resector blades may be exposed from said blade guide whereby said blades while resume the expanded shape 11 of their memory.

Figure 3A:
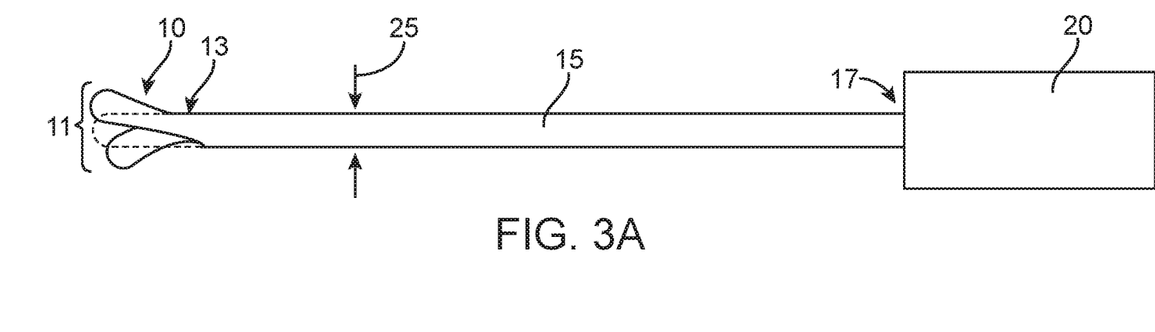
FIGS. 3A through 3D show some aspects of exemplary implementations of a device and method of insertion of an extendable memory blade into a cannula.
Figure 3B:
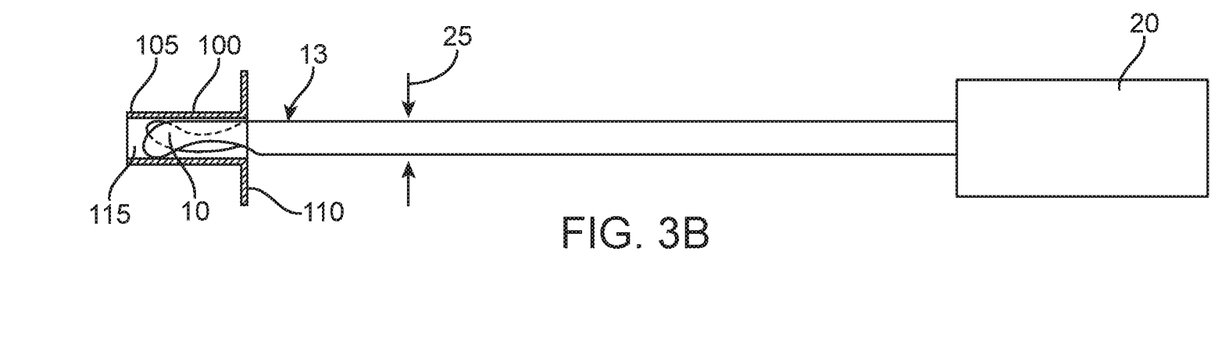
Figure 3C:
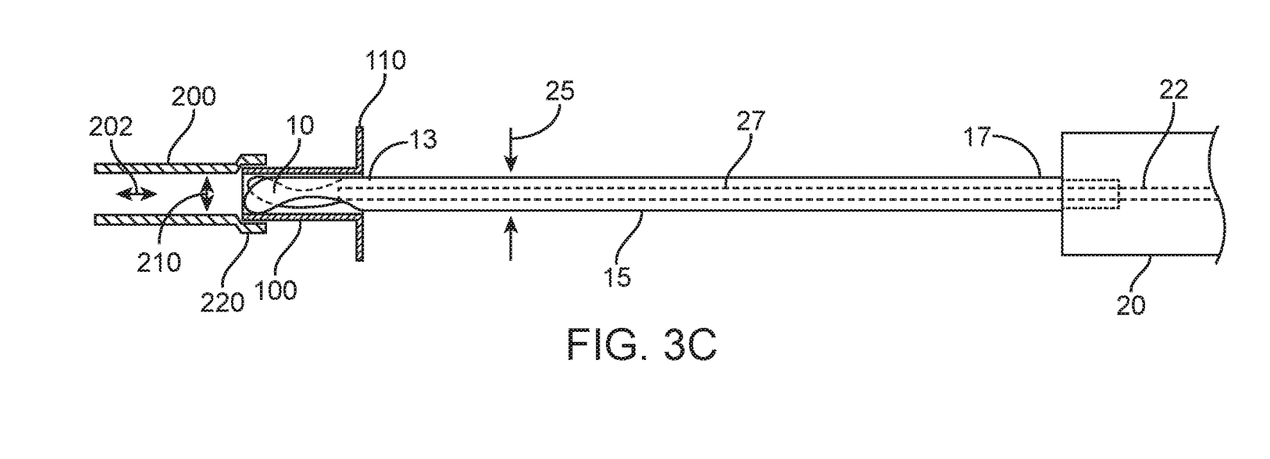

Aligning said distal end 105 of the sheath with the proximal end 220 of the cannula and positioning the compacted memory resector blades 10 in line with the cannula 200 which has an inner guide pathway 202 may be enhanced by way of an extended collar 225 at the proximal end 220 of the cannula 200. Said distal end 105 of said sheath 100 is illustrated in FIG. 3C fit into said collar 225 whereby the blade guide 115 associated with the sheath is aligned with the inner guide pathway 202 thereby facilitating a transition of the compacted blades 10 from the sheath (remaining in a compacted state) into the inner guide pathway 202 of the cannula. The distal end 230 of the cannula may form a trocar.

Figure 3D:
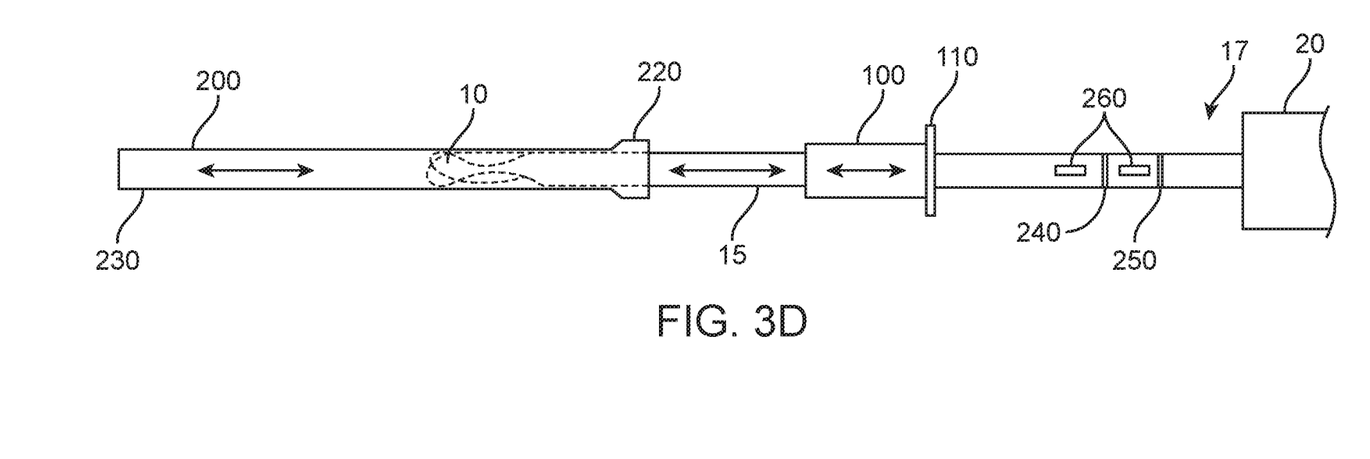

As shown in FIG. 3D after the compacted resector blades 10 (former preloaded in said sheath) have been transitioned (or transferred) to the inner guide pathway 202 of the cannula the sheath 100 may be slid along the blade body assembly 15. In some instances the sheath may also be used as a visual tool to gauge positioning of the blade 10(s). For example, visual marks, such as lines, may be placed at intervals on the blade body assembly whereby positional information of the blade(s) relative to the distal end 230 of the cannula may be known. A first mark 240 may identify when the blade(s) is positioned at the end of the distal end 230 of the cannula. A second mark 250 may identify when the blade(s) is fully deployed (thereby beyond the restraints of the cannula inner guide pathway 202) and able to expand to its memory position. A third mark 260 may be placed horizontal on the blade body assembly. Said third mark may be utilized to show the general plane or area the blades will expand. This type of mark is useful to position the blade(s) in a particular horizontal, vertical or diagonal orientation relative to the bone stricture it is used to resect.

A sequence of loading the resector blade into a cannula is as follows; a memory blade resecting tool (which may be comprised of one or more curved or extendable blades preferably constructed of nitinol or another memory alloy) is compacted and preloaded into a hollow sheath. The hollow sheath has an i.d. in that is no greater than the i.d. of the hollow cannula into which the resecting blade or tool will be inserted. The sheath and cannula are aligned with each opening (also referred to as a guide or guide pathway) whereby the compacted blade(s) may pass in a compacted form from the sheath 100 to the cannula 200.

Figure 4:
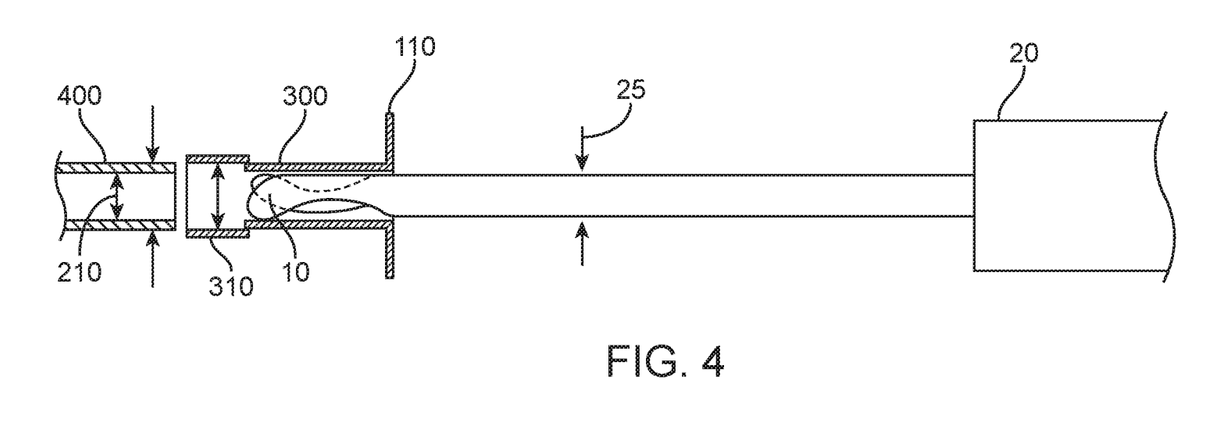
FIG. 4 shows a variation of some aspects of exemplary implementations of a device and method of insertion of an extendable memory blade into a cannula.

A sequence of loading the resector blade into a cannula is as follows; a memory blade resecting tool (which may be comprised of one or more curved or extendable blades preferably constructed of nitinol or another memory alloy) is compacted and preloaded into a hollow sheath 300 with a collar 310, as illustrated in FIG. 4. The hollow sheath has an internal diameter i.d. that is no greater than the i.d. of the hollow cannula 400 into which the resecting blade or tool will be inserted. The sheath has a sleeve (such as an annular wall) formed at its distal lend 115 with a second internal diameter (i.d.2.) which is large enough to snuggly slip over the proximal end 410 of the cannula. The i.d.2. of the sheath is at least slightly larger than the outer diameter (i.d.c.) of the cannula. Said sheath and cannula are aligned with each opening (also referred to as a guide or guide pathway) whereby the compacted blade(s) may pass in a compacted form from the sheath 300 to the cannula 400.

Figure 5A:
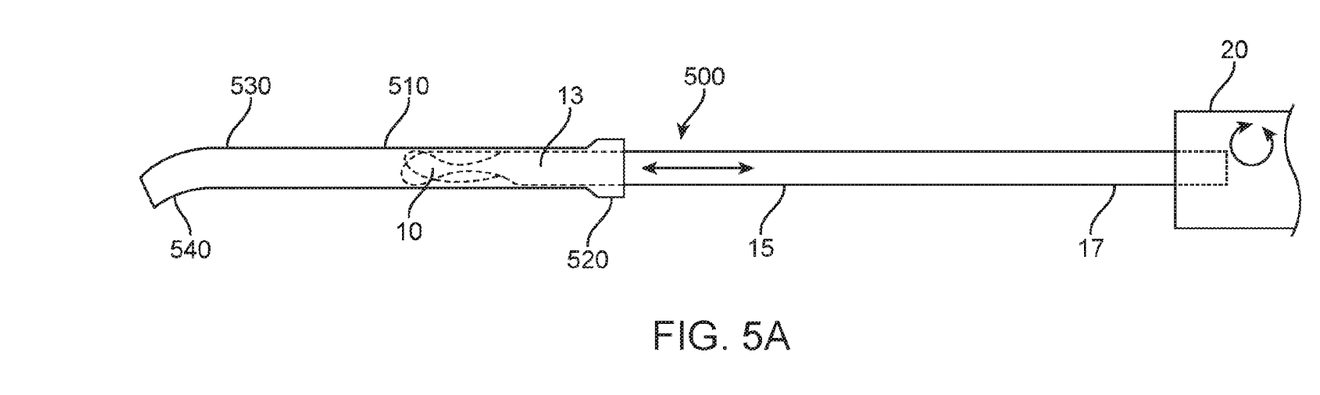
FIGS. 5A through 5C show some aspects of exemplary implementations of a device and method of insertion of a compacted extendable memory blade into an intermediary memory tip cannula which is insertable into an outer cannula.
Figure 5B:
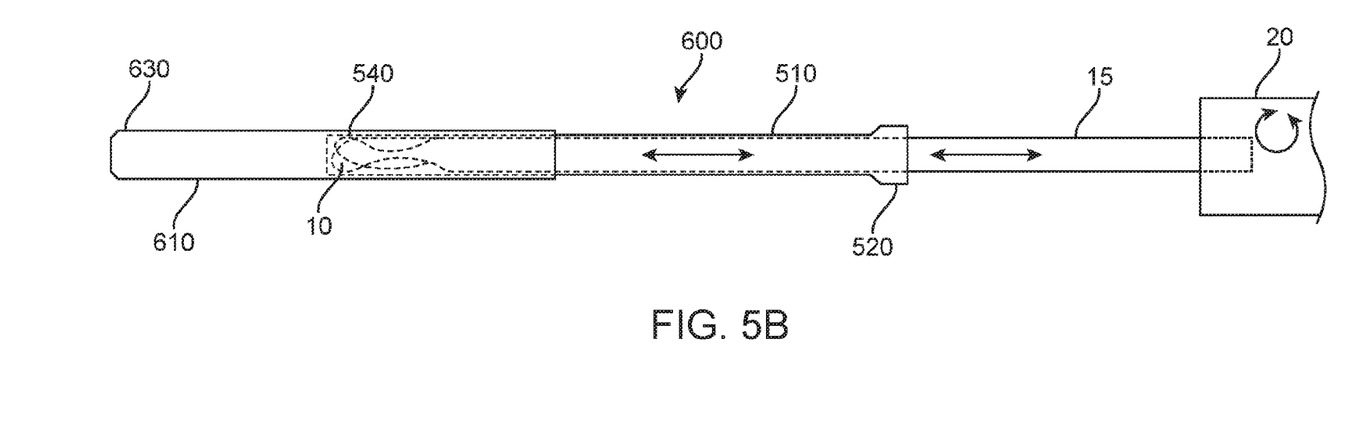
Figure 5C:
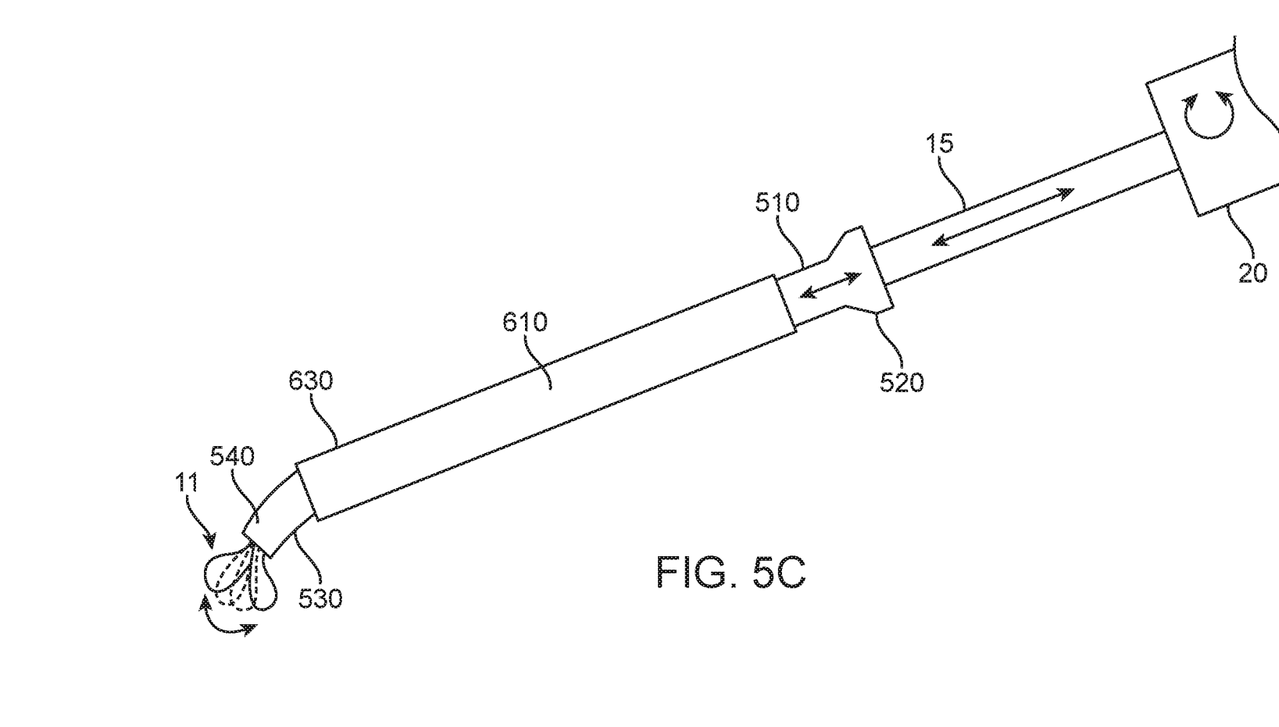
Figure 6:
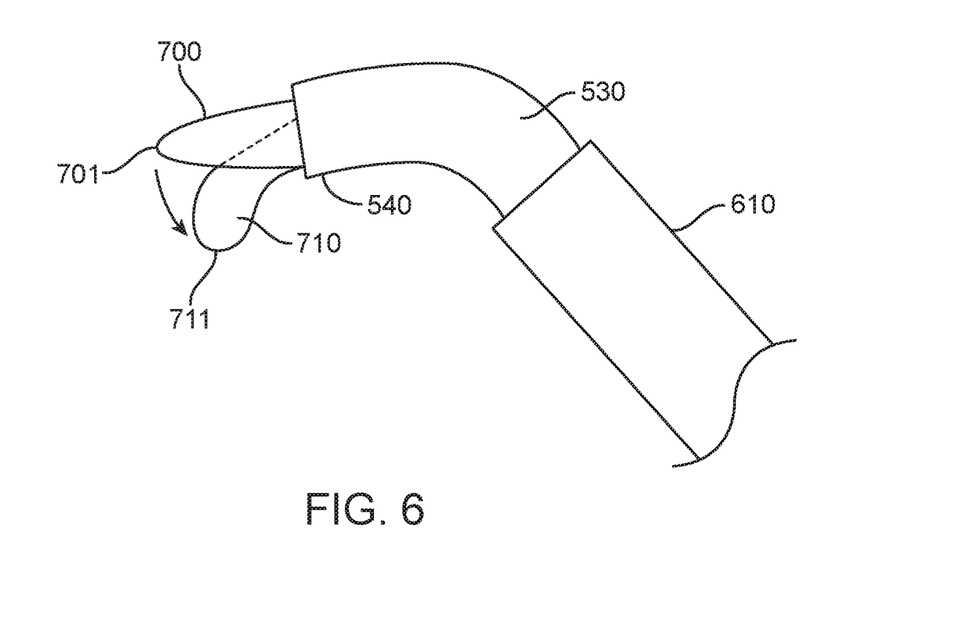
FIG. 6 shows some aspects of an exemplary implementation of a blade within an intermediary memory cannula extended from an outer cannula.

Illustrated in FIGS. 5A-5C are exemplary implementations of resecting tools and cannulas 500 and 600. In some aspects of some exemplary implementations a memory resector blade 10 or memory cutting tool is used in concert with a memory tip intermediary cannula "MTIC" 510. Said MTIC has a proximal end 520 into which a blade body assembly 15 containing a blade(s) is fitted. As previously discussed, to provide large cutting (resecting) blade(s) it is advantageous to compact or collapse memory blades or cutting tools to fit into a cannula guide (or the like) in a compressed or compacted state, and then to expand via the material memory (such a nitinol) to an expanded or larger state once beyond a distal end 530 of a cannula.

To facilitate placement of the blade(s) 10 in a correct location during use, a curved memory tip 540 may be formed at or near the distal end 530 of the MTIC 510 as part of said MTIC. Said curved memory tip 540 may be loaded into a generally straight outer cannula "OC" 610 whereby the curved tip is straightened to minimize the diameter of the outer cannula 610. The curved memory tip is inserted into the proximal end 620 of the OC. The MTIC 510 may be preloaded with the BBA 15 or it may be inserted without the BBA 15. The distal end 630 of the OC 610 may also be formed to operate as a trocar for bone cutting or puncture.

Once the distal end 630 of the OC is positioned for resection, operation, aspiration, irrigation, addition of cement or material, or drugs then the distal end 530 of the MTIC may be extended out of the distal tip 630 of the OC. Upon exit of the distal tip of the OC said curved memory tip 540 will conform to its memory shape thereby curving. Once the curved memory tip is properly placed for use, the memory resector blade(s) may be extended out of the distal end 530 and curved memory tip 540 of the MTIC 510 whereby the resector blades will extend to the expanded resector blade memory position 11.

The before mentioned discussion on aligning the memory blade(s), the preloading of the blades with the sheath, and the positioning of the blades relative to the bone are equally applicable to the above implementations.

FIGS. 6, 7, 8, 9 and 10 illustrate aspects of exemplary implementations with alternative blade(s) or tools. Some of the tools cut (or resect), some push or compress, and others scoop or relocate material. A single guide probe (which may also be used to push and retract) 700 with a distal edge 701 is shown extending form the curved memory tip 540 of the MTIC 510, which extends from the OC 610. A single blade 710 with a distal edge 711 is shown next to the probe 700. The single blade 710 scissors next to and against the probe 700 when expanding to its memory shape. By scissoring instead of gripping or clamping the probe (which has a flat surface facing the blade) 710 is used to scrape debris off the blade 710 during withdrawal of the resector blade 710 back into the MTIC 510. In some instances, a single extendable blade 750 without a separate probe may be advantageous. In some instances, the single blade 750 may act as a probe when partially extended and act as a resector when further extended.

Figure 7:
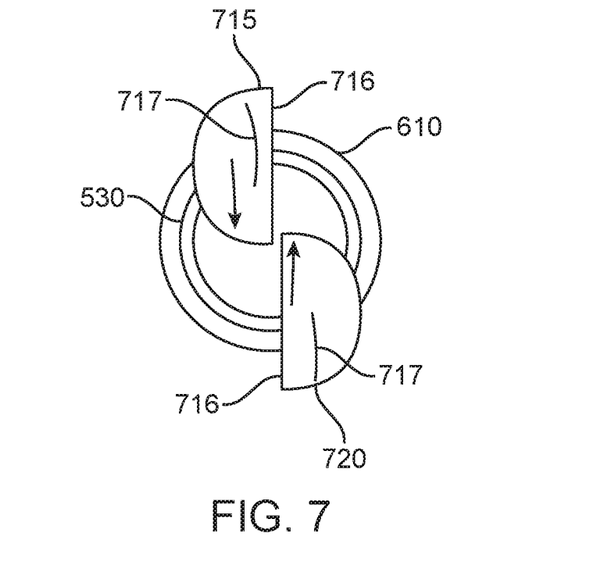
FIG. 7 shows show some aspects of exemplary implementations of memory blades extended partially from an intermediary memory cannula extended from an outer cannula.

A double blade is shown extending from the curved memory tip 540 of the MITC 510, which extends from the OC 610. The first blade 715 is shown next to the second blade 720. Both blades are memory resector blades. Each blade has a flat region 716 and a distal tip 717. The blades each scissor apart (rotate with fixed ends at the distal end of the BBA) from each other when expanding to their memory positioning. The scissor movement, as previously described, is used to scrape debris off the blades 715 and 720 during withdrawal of the resector blades. Pinching or gripping blade arrangements which have gaps between blades or tool during expansion are to be avoided, as they are more likely to jam or otherwise prevent compaction and compression of the blades, which is necessary for withdrawal into the MITC.

Figure 8:
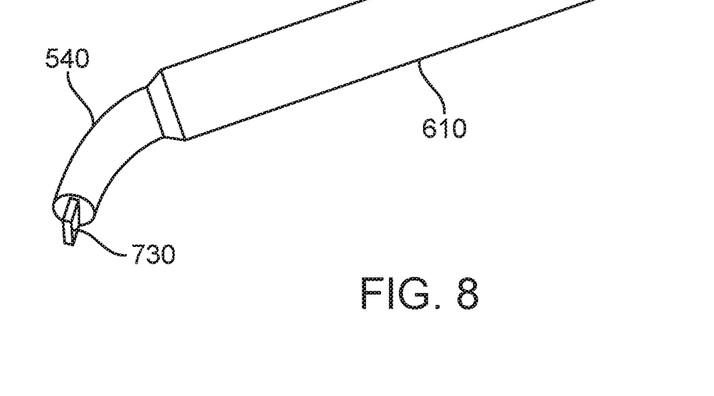
FIG. 8 shows show some aspects of exemplary implementations of a tool extended partially from an intermediary memory cannula extended from an outer cannula.
Figure 9:
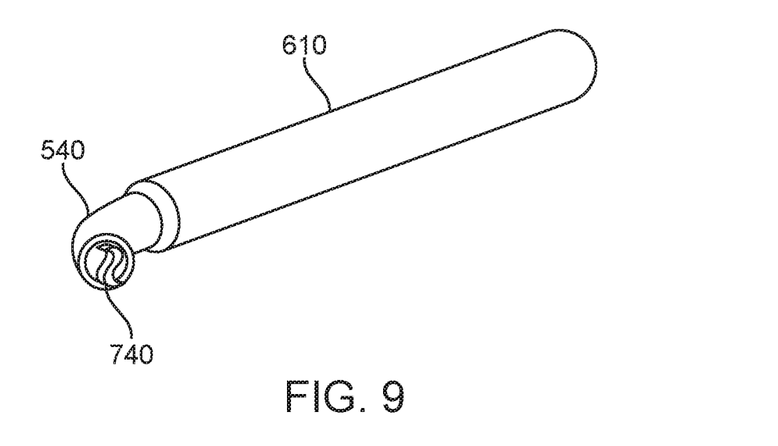
FIG. 9 shows some aspects of exemplary implementations of a tool extended partially from an intermediary memory cannula extended from an outer cannula.
Figure 10:
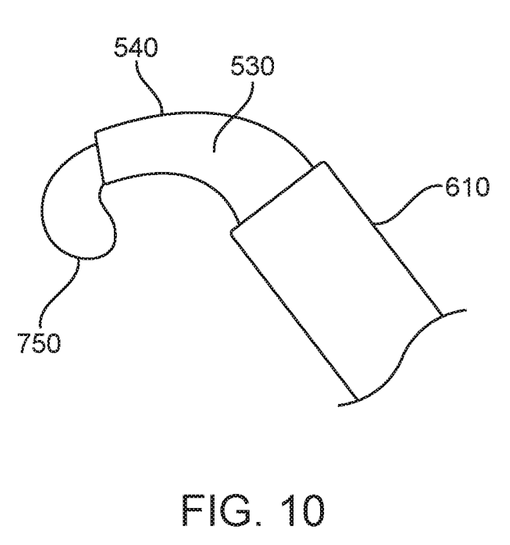
FIG. 10 shows some aspects of an exemplary implementation of a blade within an intermediary memory cannula extended from an outer cannula.

Probes which also may be scoops or single cutting tools 730 and 740 are illustrated extended from a MITC in FIGS. 8 and 9.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure, both independently and as an overall system, and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising," are intended to imply the inclusion of a stated element or step or group of elements or steps, but not the exclusion of any other element or step or group of elements or steps.

Such terms should be interpreted in their most expansive forms so as to afford the applicant the broadest coverage legally permissible.

It should be noted that the bearings may be adjusted to correspond to the intended usage. A highly lubricous material may be used, a ball shape, cone, cylinder or ovoid.

The invention claimed is:

1. A method of delivering a memory resector tool comprising:
    providing a memory blade resecting tool, having at least one resector blade and a second structure attached to a blade body assembly having an exterior surface;
    said at least one resector blade having a first substantially flat surface formed at the distal end of said blade body assembly and proximate to a second substantially flat surface in the second structure;
    said first substantially flat surface and said second substantially flat surface configured to scissor against each other during withdrawal of the at least one resector blade;
    providing a hollow sheath;
    compacting said memory blade resecting tool into said hollow sheath;
    providing a hollow cannula having a proximal end;
        the cannula having an interior diameter substantially the same as the internal diameter of said hollow sheath; and,
    aligning the hollow sheath with the cannula and passing the compacted blade resecting tool, in a compacted state, into said cannula.

2. The method of claim 1, wherein said second structure of the memory blade resecting tool is a second resector blade.

3. The method of claim 1, wherein said second structure of the memory blade resecting tool is a probe.

4. The method of claim 1, wherein said sheath may move freely up said blade body assembly.

5. The method of claim 1, wherein the memory resector tool further comprises one or more visual marks placed at intervals on the exterior of said blade body assembly whereby the position of the blade relative to the distal end of the cannula may be determined.

6. A resecting tool comprising:
    a hollow sheath with an internal diameter;
    a blade body assembly with a proximal end, a distal end, and an exterior surface within the internal diameter of the hollow sheath;
    a first memory blade having a first substantially flat surface and a second memory blade having a second substantially flat surface, the first and second substantially flat surfaces facing each other, the first and second memory blades formed at the distal end of the blade body assembly; and,
    wherein said first and second memory blades are in a compacted state when the distal ends of the first and second memory blades are within the internal diameter of the hollow sheath and said first and second memory blades are in an expanded state when the distal ends of the first and second memory blades are beyond said internal diameter;
    wherein said first and second memory blades are configured to scissor apart from each other when moving from the compacted state to the expanded state, with the first and second substantially flat surfaces scraping across each other.

7. The resecting tool of claim 6, further comprising:
    a cannula aligned with said hollow sheath; and,
    said cannula having an internal diameter substantial the same as the internal diameter of the hollow sheath whereby said first and second memory blades may be transferred from said sheath to said cannula while in the compacted state.

8. The resecting tool of claim 7, wherein said first and second memory blades are in a compacted state when the distal ends of the first and second memory blades are within the internal diameter of the cannula and the first and second memory blades are in the expanded state when the distal ends of the first and second memory blades are beyond the internal diameter of the cannula.

9. The resecting tool of claim 7, wherein said hollow sheath is moveable along said blade body assembly.

10. The resecting tool of claim 9, further comprising one or more visual marks placed at intervals on the exterior surface of said blade body assembly, wherein the position of the first and second memory blades relative to the distal end of the cannula may be determined by the location of one or more visual marks in relationship to at least one of said hollow sheath and said blade body assembly.

* * * * *